United States Patent
Kollgaard et al.

(10) Patent No.: US 8,869,621 B2
(45) Date of Patent: Oct. 28, 2014

(54) GEOMETRY COMPENSATING TRANSDUCER ATTACHMENTS FOR ULTRASONIC INSPECTION OF CHAMFERS OR COUNTERSUNK SURFACES

(75) Inventors: Jeffrey R. Kollgaard, Seattle, WA (US); Barry A. Fetzer, Renton, WA (US); Christopher R. Brown, Seattle, WA (US); William J. Tapia, Graham, WA (US); David Brooks, Seattle, WA (US)

(73) Assignee: The Boeing Company, Chicago, IL (US)

( * ) Notice: Subject to any disclaimer, the term of this patent is extended or adjusted under 35 U.S.C. 154(b) by 624 days.

(21) Appl. No.: 13/156,154

(22) Filed: Jun. 8, 2011

(65) Prior Publication Data

US 2012/0174674 A1  Jul. 12, 2012

Related U.S. Application Data

(63) Continuation-in-part of application No. 12/363,742, filed on Jan. 31, 2009, now Pat. No. 8,286,487.

(51) Int. Cl.
| | |
|---|---|
| *G01N 29/28* | (2006.01) |
| *G01N 29/24* | (2006.01) |
| *G01N 29/22* | (2006.01) |
| *G01K 11/02* | (2006.01) |

(52) U.S. Cl.
CPC .............. *G01N 29/225* (2013.01); *G01N 29/28* (2013.01); *G01N 2291/0258* (2013.01); *G01N 29/2487* (2013.01); *G01K 11/02* (2013.01); *G01N 2291/0231* (2013.01)
USPC ..................... 73/598; 73/600; 73/627; 73/588

(58) Field of Classification Search
USPC .................... 73/584, 588, 598, 600, 627, 629
See application file for complete search history.

(56) References Cited

U.S. PATENT DOCUMENTS

| | | | | |
|---|---|---|---|---|
| 3,512,400 | A * | 5/1970 | Lynnworth | ..................... 73/597 |
| 7,222,514 | B2 | 5/2007 | Kollgaard et al. | |
| 2007/0165918 | A1* | 7/2007 | Howard | ......................... 382/128 |

OTHER PUBLICATIONS

"Module Curve Tool", http://www.trainweb.org/freemoslo/Modules/Tips-and-Techniques/module_curve_tool.htm, Aug. 15, 2002.*

* cited by examiner

*Primary Examiner* — Paul West
(74) *Attorney, Agent, or Firm* — Hanley, Flight and Zimmerman, LLC

(57) ABSTRACT

A geometry compensating transducer attachment for ultrasonic inspection of a structure includes a geometry-compensating structure having at least one angled surface configured to engage the structure to be inspected, and the geometry-compensating structure having an acoustic velocity generally matching an acoustic velocity of the structure to be inspected.

16 Claims, 5 Drawing Sheets

GEOMETRY COMPENSATING TRANSDUCER ATTACHMENTS FOR ULTRASONIC INSPECTION OF CHAMFERS OR COUNTERSUNK SURFACES

CROSS REFERENCE TO RELATED APPLICATIONS

This application is a continuation-in-part application of a U.S. patent application Ser. No. 12/363,742, filed on Jan. 31, 2009 now U.S. Pat. No. 8,286,487, and entitled "ULTRASONIC APERTURE SCANNING SYSTEM AND METHOD" which is incorporated herewith for reference in its entirety.

TECHNICAL FIELD

The disclosure generally relates to ultrasonic inspection of structures such as composite structures. More particularly, the disclosure relates to geometry compensating transducer attachments which eliminate or reduce refraction and scattering in ultrasonic inspection of laminar structures having chamfers or countersunk surfaces.

BACKGROUND

In aerospace and other industries it may be occasionally necessary to inspect structures for the presence of irregularities in the structures. Ultrasonic inspection is a technique which is extensively used to inspect composite and other structures for irregularities, since the irregularities tend to be laminar in nature and located parallel to the overlying sound-entry interface (an optimum orientation for ultrasonic detection). However, ultrasonic inspection of irregularities beneath angled interfaces such as chamfers and countersunk surfaces may not be accurate since those types of surfaces tend to refract and scatter the ultrasonic beams which are emitted through the interfaces. Flush fastener holes, existing in the thousands on a typical aircraft, represent a common angled interface, one that is subject to inspection to identify damage caused by drilling or fastener removal.

A variety of methods have been devised to minimize the undesirable effects of refraction and scattering which are caused by angled interfaces in a structure subjected to ultrasonic inspection. One method includes positioning of ultrasonic transducers parallel to the surface of a composite structure and at an angle to the plies of the structure. The ultrasonic beam enters the structure and is channeled by the fibers in the plies. Laminar irregularities in the plies do not return an ultrasonic echo, thus failing to reveal the presence of the irregularities.

Another method involves positioning of ultrasonic transducers parallel to the plies in the structure on a plastic wedge. Due to the velocity difference between the plastic wedge and the carbon fiber material, the ultrasonic beam refracts at an angle to the plies. Laminar irregularities in the plies do not return an ultrasonic echo, thus failing to reveal the presence of the irregularities.

Some solutions have entailed shaped ultrasonic arrays to sweep sound beams through the material. However, these techniques may still produce marginal echo returns from delaminations in the plane of the plies. In other cases, ultrasonic inspection can be performed from a parallel back surface toward the angled surface, but in many such cases, access to the back side of the structure is not possible.

Over the years, efforts have been made without success to identify a material that matches the acoustic characteristics of carbon fiber laminate. Due to the ultrasonic velocity and acoustic impedance mismatch between those materials and carbon fiber laminate, those materials will cause refraction and interface energy loss when used as a geometry compensator. With some materials, a suitably-chosen angled transducer interface can result in a perpendicular beam in the laminate, however the acoustic impedance losses due to dissimilar materials at the interface remain. It has been found that a CFRP (Carbon Fiber Reinforcement Polymer) wedge-shaped or plug-shaped transducer attachment essentially restores the structure being inspected to a plate-like configuration, thereby greatly simplifying ultrasonic inspection. The bond line interface between the wedge or plug attachment and the structure has a negligible effect on the ultrasonic beam since there is no refraction or acoustic impedance loss.

Therefore, geometry compensating transducer attachments which eliminate or reduce refraction and scattering in ultrasonic inspection of structures having chamfers or countersunk surfaces are needed.

SUMMARY

The disclosure is generally directed to a geometry compensating transducer attachment for ultrasonic inspection of a structure. The geometry compensating transducer attachment includes a geometry-compensating structure having at least one angled surface configured to engage the structure to be inspected, and the geometry-compensating structure having an acoustic velocity and impedance generally matching the acoustic velocity and impedance of the structure to be inspected.

In some embodiments, the geometry compensating transducer attachment may include a geometry-compensating structure having at least one angled surface configured to engage the structure to be inspected, the geometry-compensating structure having an acoustic velocity and impedance generally matching an acoustic velocity and impedance of the structure to be inspected; an ultrasonic transducer disposed in contact with the geometry-compensating structure; and an indicator unit interfacing with the ultrasonic transducer.

The disclosure is further generally directed to an ultrasonic inspection method. An illustrative embodiment of the ultrasonic inspection method includes providing a structure to be inspected having a sloped surface; providing a geometry-compensating structure having at least one angled surface configured to engage the sloped surface on the structure to be inspected, the geometry-compensating structure having an acoustic velocity and impedance generally matching an acoustic velocity and impedance of the structure to be inspected; placing the angled surface of the geometry-compensating structure against the sloped surface of the structure to be inspected; transmitting an ultrasonic beam through the geometry-compensating structure into the structure to be inspected; receiving the ultrasonic beam; and interpreting results based on receiving the ultrasonic beam.

BRIEF DESCRIPTION OF THE ILLUSTRATIONS

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the claims. Furthermore, there is no intention to be bound by any expressed or implied theory presented in the preceding technical field, background, brief summary or the following detailed description.

Figure 1:
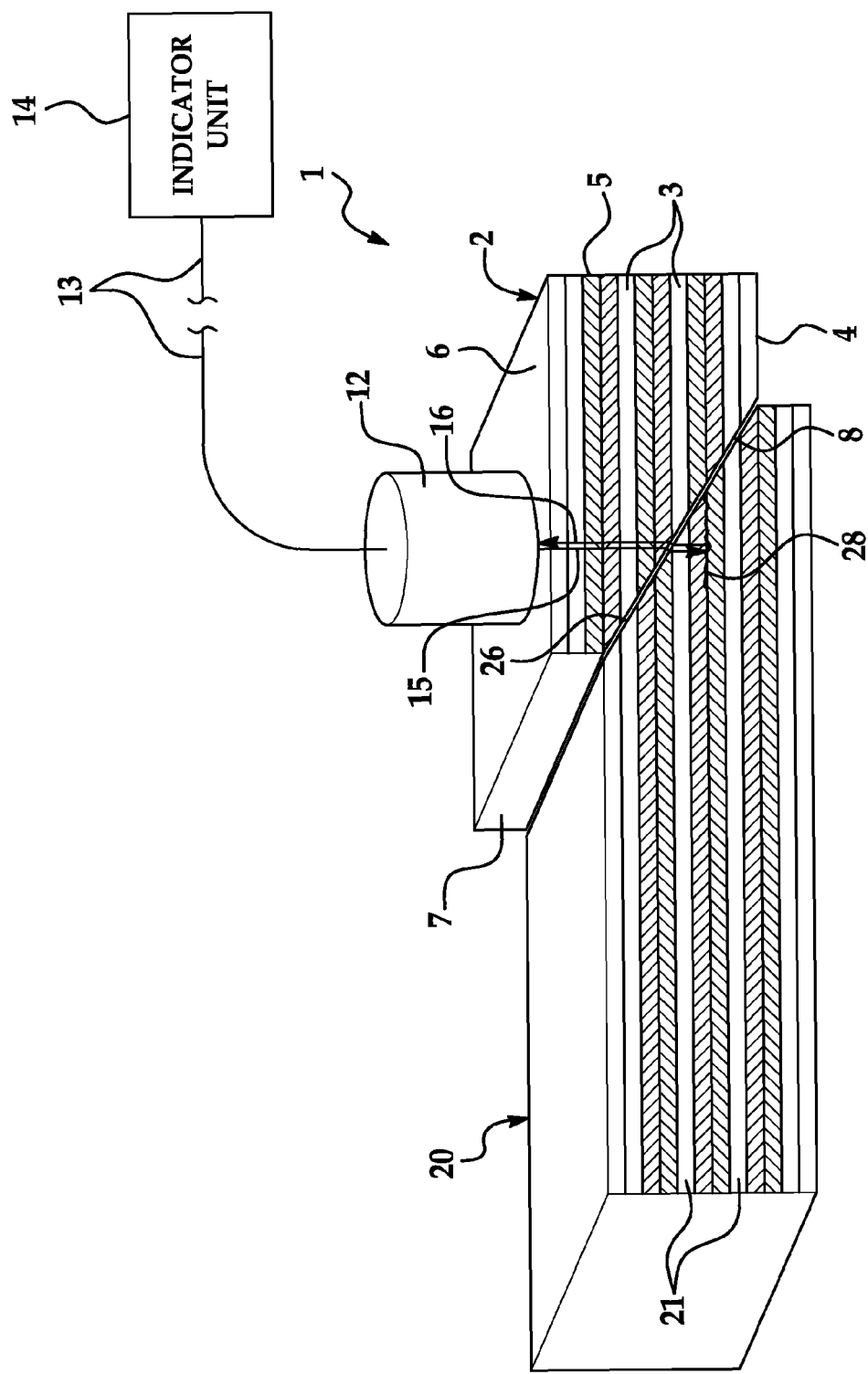
FIG. 1 is a perspective view which illustrates ultrasonic inspection of a structure with a chamfer using an illustrative geometry-compensating wedge.

Referring initially to FIG. 1, an illustrative embodiment of a geometry compensating transducer attachment, hereinafter attachment, is generally indicated by reference numeral 1. The attachment 1 may include a geometry-compensating wedge 2. The geometry-compensating wedge 2 may be non-metallic. In some embodiments, the geometry-compensating wedge 2 may be a composite material and may include laminated composite plies 3. The geometry-compensating wedge 2 may include a bottom wedge surface 4, side wedge surfaces 5 and 7 and a top wedge surface 6. The geometry-compensating wedge 2 may have at least one angled surface 8. In some embodiments, an angled wedge surface may extend between the bottom wedge surface 4 and the side wedge surface 7.

The attachment 1 may be used to carry out ultrasonic inspection of a structure 20 as will be hereinafter described. The ultrasonic velocity (speed of acoustic transmission through the geometry-compensating wedge 2) may approximate or generally match the ultrasonic velocity of the structure 20 which is to be inspected. In some embodiments, the structure 20 may be non-metallic. In some embodiments, the structure 20 may be a composite material and may include laminated composite plies 21. The structure 20 may include a chamfer 26 the slope or angle of which generally matches or corresponds to the slope or angle of the complementary angled wedge surface 8 of the geometry-compensating wedge 2 of the attachment 1. An irregularity 28 such as a delamination, for example and without limitation, may exist in the structure 20 beneath the chamfer 26. In some embodiments, the geometry-compensating wedge 2 and the structure 20 which is to be inspected may be the same or substantially the same material.

An ultrasonic transducer 12 may be placed against the top wedge surface 6 of the geometry-compensating wedge 2. An indicator unit 14 may be connected to the ultrasonic transducer through transducer wiring 13 or other suitable connection. An incident ultrasonic beam 15 may be transmitted from the ultrasonic transducer 12. The incident ultrasonic beam 15 may transmit through the interface which is formed by the angled wedge surface 8 on the geometry-compensating wedge 2 and the chamfer 26 on the structure 20 to the irregularity 28 in the structure 20. A reflected ultrasonic beam 16 may be reflected from the irregularity 28 through the interface between the chamfer 26 and the angled wedge surface 8 back to the ultrasonic transducer 12. Based on the modified characteristics of the reflected ultrasonic beam 16 relative to the incident ultrasonic beam 15, the indicator unit 14 may indicate the presence of the irregularity 28 beneath the chamfer 26 on the structure 20.

It will be appreciated by those skilled in the art that the geometry-compensating wedge 2 of the attachment 1 essentially restores the structure 20 which is being inspected to a plate-like configuration, thereby greatly simplifying ultrasonic inspection. Because the geometry-compensating wedge 2 of the attachment 1 is substantially matched to the ultrasonic velocity and acoustic impedance of the structure 20, the incident ultrasonic beam 15 and the reflected ultrasonic beam 16 enter and reflect perpendicular to the carbon composite plies 21 in the structure 20 without refraction and scattering. Therefore, the bond line interface which is formed by the angled wedge surface 8 and the chamfer 26 has a negligible effect on the incident ultrasonic beam 15 and the reflected ultrasonic beam 16.

Figure 2:
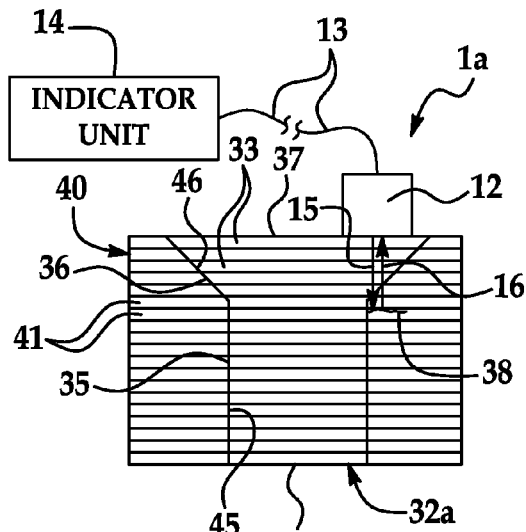
FIGS. 2-4 are cross-sectional views which illustrate ultrasonic inspection of structures with a countersunk surface using illustrative geometry-compensating plugs of various sizes.
Figure 3:
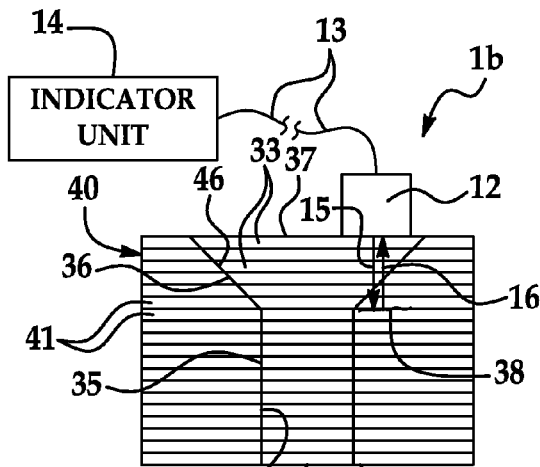
Figure 4:
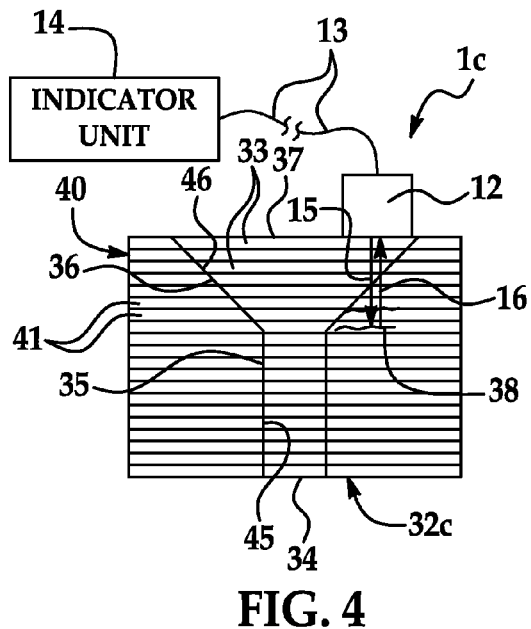

Referring next to FIGS. 2-4, an alternative illustrative embodiment of the geometry-compensating transducer attachment, hereinafter attachment, is generally indicated by reference numeral 1a in FIG. 2. The attachment 1a may include a geometry-compensating plug 32a. The geometry-compensating plug 32a may be non-metallic. In some embodiments, the geometry-compensating plug 32a may be a composite material and may include laminated composite plies 33. The geometry-compensating plug 32a may include a bottom plug surface 34, an annular side plug surface 35 and a top plug surface 37. At least one annular angled plug surface 36 may extend between the top plug surface 37 and the side plug surface 35.

The attachment 1a may be used to carry out ultrasonic inspection of a structure 40 as will be hereinafter described. The ultrasonic velocity of the geometry-compensating plug 32a may approximate or generally match the ultrasonic velocity of the structure 40 which is to be inspected. In some embodiments, the structure 40 may be non-metallic. In some embodiments, the structure 40 may be a composite material and may include laminated composite plies 41. The structure 40 may include a countersunk opening 45 having countersunk surface 46 the slope or angle of which generally matches or corresponds to the slope or angle of the complementary angled plug surface 36 of the geometry-compensating plug 32a of the attachment 1a. An irregularity 38 such as a delamination, for example and without limitation, may exist in the structure 40 beneath the countersunk surface 46. In some embodiments, the geometry-compensating plug 32a and the structure 40 which is to be inspected may be the same or substantially the same material.

An ultrasonic transducer 12 may be placed against the top plug surface 37 of the geometry-compensating plug 32a. An indicator unit 14 may be connected to the ultrasonic transducer through transducer wiring 13 or other suitable connection. An incident ultrasonic beam 15 may be transmitted from the ultrasonic transducer 12. The incident ultrasonic beam 15 may transmit through the interface which is formed by the angled plug surface 36 on the geometry-compensating plug 32a and the countersunk surface 46 on the structure 40 to the irregularity 38 in the structure 40. A reflected ultrasonic beam 16 may be reflected from the irregularity 38 through the interface between the countersunk surface 46 and the angled plug surface 36 back to the ultrasonic transducer 12. Based on the modified characteristics of the reflected ultrasonic beam 16 relative to the incident ultrasonic beam 15, the indicator unit 14 may indicate the presence of the irregularity 38 beneath the countersunk surface 46 on the structure 40. Transducer attachments 1b and 1c having geometry-compensating plugs 32b and 32c, respectively, of correspondingly reduced size or diameter are shown in FIGS. 3 and 4.

Figure 5:
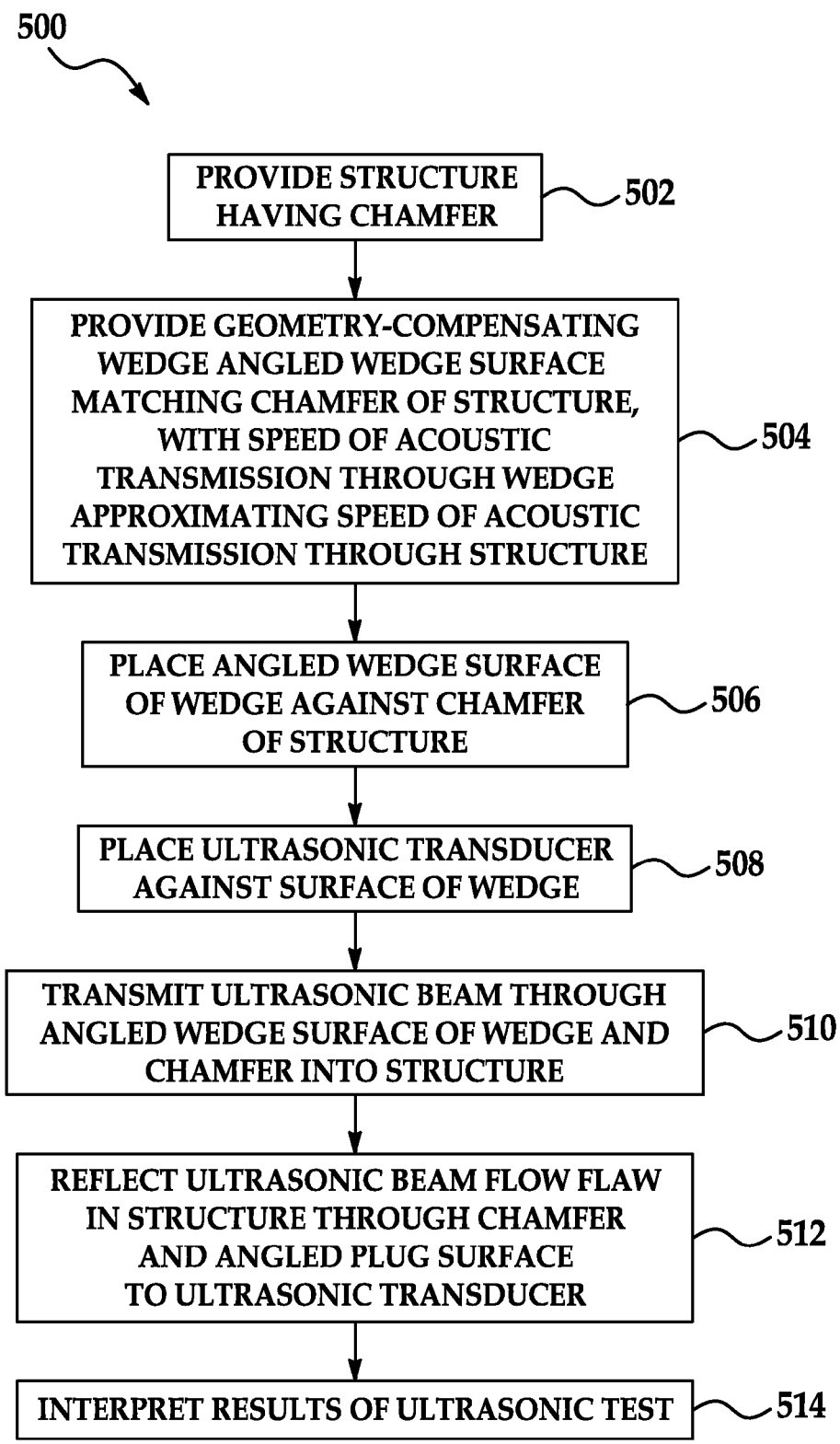
FIG. 5 is a flow diagram of an illustrative embodiment of an ultrasonic inspection method.

Referring next to FIG. 5, a flow diagram 500 of an illustrative embodiment of an ultrasonic inspection method is shown. In block 502, a structure having a chamfer is provided. In block 504, a geometry-compensating wedge having an angled wedge surface matching the chamfer of the structure is provided. The speed (acoustic velocity) of acoustic transmission through the wedge may approximate or generally match the speed of acoustic transmission through the structure. In block 506, the angled wedge surface of the wedge may be placed against the complementary chamfer of the structure. In block 508, an ultrasonic transducer may be placed against a surface of the wedge. In block 510, an ultrasonic beam may be transmitted through the angled wedge surface of the wedge and the chamfer into the structure. In block 512, the ultrasonic beam may be reflected from an irregularity in the structure and back through the chamfer and the angled wedge surface to the ultrasonic transducer. In block 514, the results of the ultrasonic test may be interpreted.

Figure 5A:
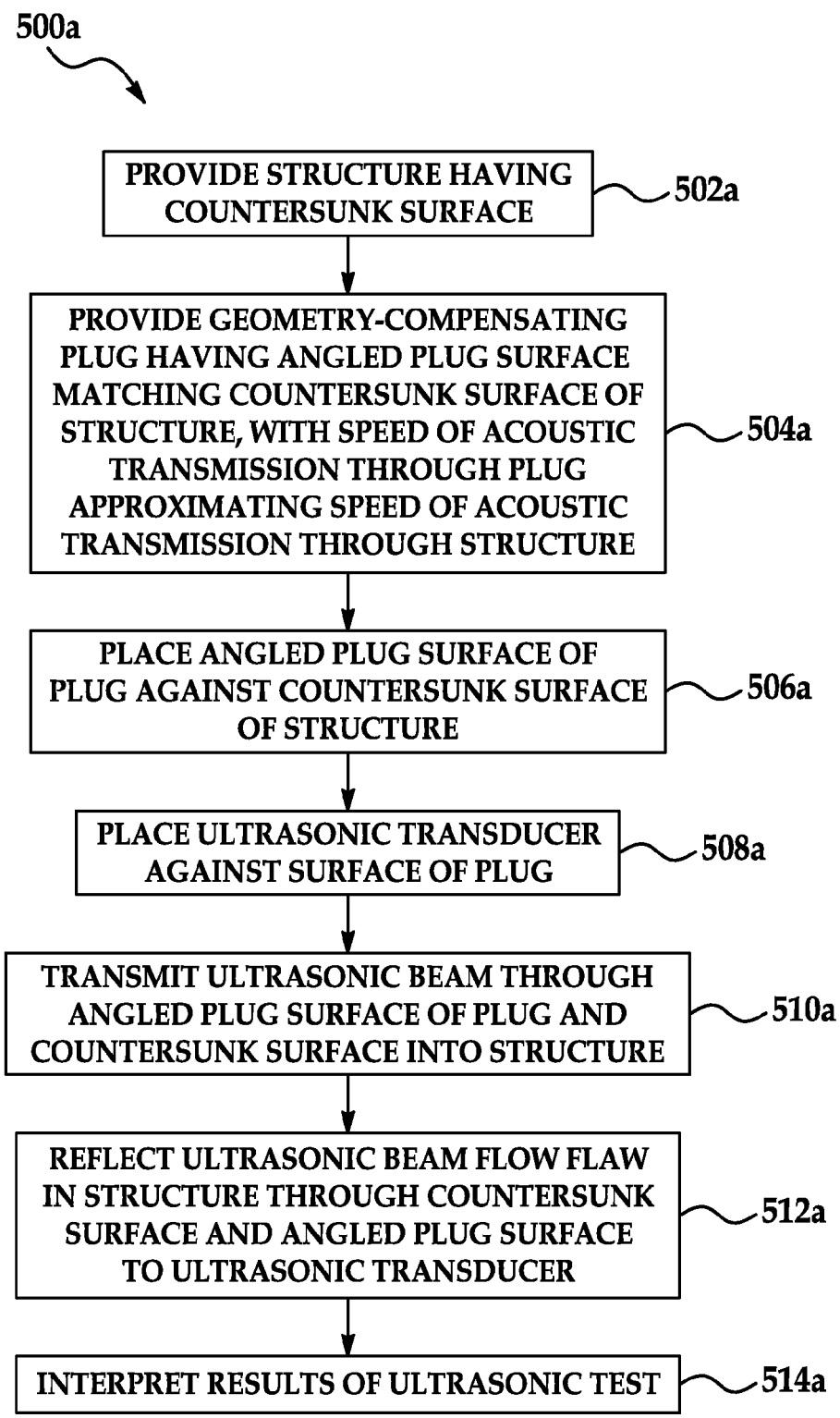
FIG. 5A is a flow diagram of an alternative illustrative embodiment of an ultrasonic inspection method.

Referring next to FIG. 5A, a flow diagram 500a of an illustrative embodiment of an ultrasonic inspection method is shown. In block 502a, a structure having a countersunk surface is provided. In block 504a, a geometry-compensating plug having an angled plug surface matching the countersunk surface of the structure is provided. The speed of acoustic transmission through the plug (acoustic velocity) may approximate or generally match the speed of acoustic transmission through the structure. In block 506a, the angled plug surface of the plug may be placed against the complementary countersunk surface of the structure. In block 508a, an ultrasonic transducer may be placed against a surface of the plug. In block 510a, an ultrasonic beam may be transmitted through the angled plug surface of the plug and the countersunk surface into the structure. In block 512a, the ultrasonic beam may be reflected from an irregularity in the structure and back through the countersunk surface and the angled plug surface to the ultrasonic transducer. In block 514a, the results of the ultrasonic test may be interpreted.

Figure 6:
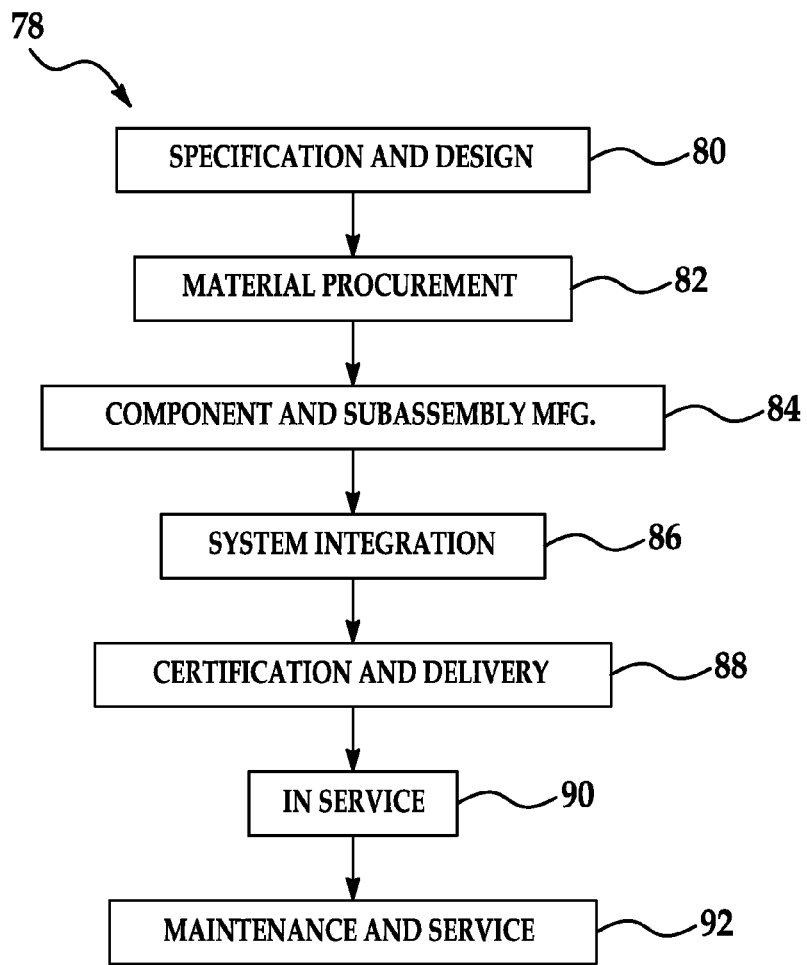
FIG. 6 is a flow diagram of an aircraft production and service methodology.
Figure 7:
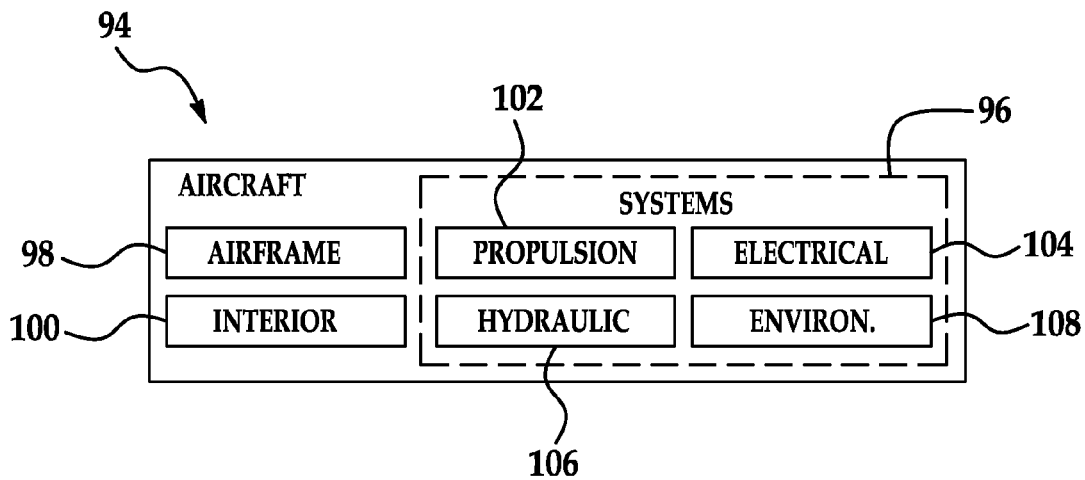
FIG. 7 is a block diagram of an aircraft.

Referring next to FIGS. 6 and 7, embodiments of the disclosure may be used in the context of an aircraft manufacturing and service method 78 as shown in FIG. 6 and an aircraft 94 as shown in FIG. 7. During pre-production, exemplary method 78 may include specification and design 80 of the aircraft 94 and material procurement 82. During production, component and subassembly manufacturing 84 and system integration 86 of the aircraft 94 takes place. Thereafter, the aircraft 94 may go through certification and delivery 88 in order to be placed in service 90. While in service by a customer, the aircraft 94 may be scheduled for routine maintenance and service 92 (which may also include modification, reconfiguration, refurbishment, and so on).

Each of the processes of method 78 may be performed or carried out by a system integrator, a third party, and/or an operator (e.g., a customer). For the purposes of this description, a system integrator may include without limitation any number of aircraft manufacturers and major-system subcontractors; a third party may include without limitation any number of vendors, subcontractors, and suppliers; and an operator may be an airline, leasing company, military entity, service organization, and so on.

As shown in FIG. 7, the aircraft 94 produced by exemplary method 78 may include an airframe 98 with a plurality of systems 96 and an interior 100. Examples of high-level systems 96 include one or more of a propulsion system 102, an electrical system 104, a hydraulic system 106, and an environmental system 108. Any number of other systems may be included. Although an aerospace example is shown, the principles of the invention may be applied to other industries, such as the automotive industry.

The apparatus embodied herein may be employed during any one or more of the stages of the production and service method 78. For example, components or subassemblies corresponding to production process 84 may be fabricated or manufactured in a manner similar to components or subassemblies produced while the aircraft 94 is in service. Also one or more apparatus embodiments may be utilized during the production stages 84 and 86, for example, by substantially expediting assembly of or reducing the cost of an aircraft 94. Similarly, one or more apparatus embodiments may be utilized while the aircraft 94 is in service, for example and without limitation, to maintenance and service 92.

Although the embodiments of this disclosure have been described with respect to certain exemplary embodiments, it is to be understood that the specific embodiments are for purposes of illustration and not limitation, as other variations will occur to those of skill in the art.

What is claimed is:

1. A geometry-compensating transducer attachment for ultrasonic inspection of a composite structure, the attachment comprising a geometry-compensating structure having at least one angled surface configured to engage the composite structure, the geometry-compensating structure comprising layers corresponding to layers of the composite structure, the layers of the geometry-compensating structure to align with corresponding layers of the composite structure when the at least one angled surface of the geometry-compensating structure engages the composite structure and the geometry-compensating structure having an acoustic velocity substantially matching an acoustic velocity of the composite structure, wherein the at least one angled surface of the geometry-compensating structure is to engage a surface of the composite structure that is angled with respect to the layers of the composite structure, and wherein the surface of the composite structure is a countersunk surface in the composite structure.

2. The geometry-compensating transducer attachment of claim 1, wherein the geometry-compensating structure is non-metallic.

3. The geometry-compensating transducer attachment of claim 1, wherein the geometry-compensating structure and the composite structure comprise substantially the same materials.

4. The geometry-compensating transducer attachment of claim 1, wherein the geometry-compensating structure comprises a geometry-compensating plug.

5. A geometry-compensating transducer attachment for ultrasonic inspection of a composite structure, the attachment comprising:
   a geometry-compensating structure having at least one angled surface to engage an angled surface of the composite structure, the angled surface of the composite structure being at an angle not parallel to composite layers of the composite structure, the geometry-compensating structure having an acoustic velocity substantially matching an acoustic velocity of the composite structure, the geometry-compensating structure to propagate an ultrasonic signal to the angled surface of the composite structure in a direction normal to the composite layers of the composite structure; and
   an ultrasonic transducer in contact with the geometry-compensating structure, the ultrasonic transducer to transmit the ultrasonic signal through the geometry-compensating structure to the structure to be inspected via an interface between the at least one angled surface of the geometry-compensating structure and the angled surface of the composite structure.

6. The geometry-compensating transducer attachment of claim 5, wherein the geometry-compensating structure is non-metallic.

7. The geometry-compensating transducer attachment of claim 6, wherein the geometry-compensating structure and the composite structure comprise substantially the same materials.

8. The geometry-compensating transducer attachment of claim 6, wherein the geometry-compensating structure comprises a geometry-compensating wedge.

9. The geometry-compensating transducer attachment of claim 6, wherein the geometry-compensating structure comprises a geometry-compensating plug.

10. The geometry-compensating transducer attachment of claim 5, wherein the layers of the geometry-compensating structure comprise a plurality of composite plies.

11. An ultrasonic inspection method, comprising:
placing an angled surface of a geometry-compensating structure against a surface of a composite structure, the surface of the composite structure being sloped with respect to layers of the composite structure, the geometry-compensating structure having at least one angled surface configured to engage the surface on the structure, the geometry-compensating structure having layers corresponding to at least a portion of the layers of the composite structure, and the geometry-compensating structure having an acoustic velocity substantially matching an acoustic velocity of the composite structure;
aligning the layers of the geometry-compensating structure with corresponding layers of the composite structure;
transmitting an ultrasonic beam through the geometry-compensating structure into the composite structure;
receiving the ultrasonic beam; and
interpreting results based on receiving the ultrasonic beam.

12. The method of claim 11, wherein the geometry-compensating structure is non-metallic.

13. The method of claim 11, wherein the layers of the composite structure and the layers of the geometry-compensating structure are the same material.

14. The method of claim 11, wherein the geometry-compensating structure comprises a wedge having at least one angled surface.

15. The method of claim 11, wherein the geometry-compensating structure comprises a plug having at least one angled surface.

16. A geometry-compensating transducer attachment for ultrasonic inspection of a composite structure, the attachment comprising a geometry-compensating structure having at least one angled surface to engage an angled surface of the composite structure, the angled surface of the composite structure being at an angle not parallel to composite layers of the composite structure, the geometry-compensating structure having an acoustic velocity substantially matching an acoustic velocity of the composite structure, the geometry-compensating structure to propagate an ultrasonic signal to the angled surface of the composite structure in a direction normal to the composite layers of the composite structure, wherein the at least one angled surface of the geometry-compensating structure is to be placed against a chamfered or sloped surface of the composite structure, the chamfered or sloped surface comprising a countersunk surface.

* * * * *